(12) United States Patent
Muser

(10) Patent No.: US 12,171,476 B2
(45) Date of Patent: Dec. 24, 2024

(54) EASY START CANNULATED BONE SCREW

(71) Applicant: Conmed Corporation, Largo, FL (US)

(72) Inventor: Andrew P. Muser, St. Pete Beach, FL (US)

(73) Assignee: Conmed Corporation, Largo, FL (US)

( * ) Notice: Subject to any disclaimer, the term of this patent is extended or adjusted under 35 U.S.C. 154(b) by 42 days.

(21) Appl. No.: 18/053,581

(22) Filed: Nov. 8, 2022

(65) Prior Publication Data

US 2023/0065021 A1    Mar. 2, 2023

Related U.S. Application Data

(63) Continuation of application No. 16/764,634, filed as application No. PCT/US2018/053412 on Sep. 28, 2018, now Pat. No. 11,490,938.

(60) Provisional application No. 62/599,228, filed on Dec. 15, 2017, provisional application No. 62/569,770, filed on Oct. 9, 2017.

(51) Int. Cl.
*A61B 17/86* (2006.01)

(52) U.S. Cl.
CPC .......... *A61B 17/864* (2013.01); *A61B 17/863* (2013.01); *A61B 17/8635* (2013.01)

(58) Field of Classification Search
CPC ........................... A61B 17/8635; A61B 17/864
See application file for complete search history.

(56) References Cited

U.S. PATENT DOCUMENTS

| 2013/0211468 A1* | 8/2013 | Huebner .............. A61B 17/863 606/328 |
| 2013/0253594 A1 | 9/2013 | Zucherman et al. |
| 2015/0196336 A1 | 7/2015 | Whipple et al. |
| 2016/0310187 A1 | 10/2016 | Leibinger et al. |

FOREIGN PATENT DOCUMENTS

| JP | 2013503663 A | 2/2013 |
| JP | 2020536635 A | 12/2020 |
| WO | 2017085376 A1 | 5/2017 |

OTHER PUBLICATIONS

KR Office Action, Application No. 10-2022-7045436, dated Sep. 26, 2023, entire document.
Translated Japanese Office Action, Application No. 2022-161136, dated Jan. 22, 2024, pp. 1-11.
EP Communication 94(3) EPC, App. No. 18797210.4, Dated Jan. 16, 2023, pp. 1-6.

* cited by examiner

*Primary Examiner* — Olivia C Chang
(74) *Attorney, Agent, or Firm* — Bond, Schoeneck & King, PLLC; Frederick J. M. Price

(57) ABSTRACT

A surgical screw for fixation into bone or soft tissue. The surgical screw includes a cannulated body having a proximal end and a distal end. The distal end of the cannulated body has a tapered tip and a plurality of threads extend around the exterior of the cannulated body. An introducer extends distally from the tapered tip and has a diameter (which can be variable or constant) which is less than a diameter of the tapered tip. The surgical screw is cannulated such that a channel extends through the body from the proximal end to (and sometimes through) the distal end.

13 Claims, 13 Drawing Sheets

EASY START CANNULATED BONE SCREW

CROSS-REFERENCE TO RELATED APPLICATIONS

This application is a continuation of U.S. patent application Ser. No. 16/764,634 filed on May 15, 2020 (now U.S. Pat. No. 11,490,938) which is a National Stage Application under 35 U.S.C. 371 based on International Patent Application PCT/US18/53412 filed on Sep. 28, 2018 which claims priority to U.S. Provisional Patent Application Ser. No. 62/569,770, filed on Oct. 9, 2017 and entitled "Easy Start Cannulated Bone Screw," and U.S. Provisional Patent Application Ser. No. 62/599,228, filed on Dec. 15, 2017 and entitled "Easy Start Cannulated Bone Screw," the entireties of which are incorporated herein by reference.

BACKGROUND OF THE INVENTION

1. Field of the Invention

The present disclosure is directed generally to a surgical fixation device and, more particularly, to a cannulated screw for fixation into bone or soft tissue.

2. Description of Related Art

In orthopedic surgeries, screws are often used to secure and fix biological material or another object, such as an implant, in a desired position relative to a bone. For example, screws are used to attach a bone block to an existing bone or to secure soft tissue to a bone or soft tissue. The initial threading of the screw into the bone or a bone block can be difficult. Therefore, in some procedures, a pilot hole is required to aid in alignment of the screw. As well understood in the surgical field, the pilot hole is smaller in depth and diameter than the screw to provide a guide for the screw, while still being narrow enough to allow enough of the threads of the screw to penetrate the boney interference site. A mallet may also be used to hammer the screw deep enough for the threads to penetrate the boney interference site.

Drilling a pilot hole requires additional surgical time and additional surgical instruments. While using a mallet to hammer the screw into the bone may be less time consuming and require less instrumentation, it is less precise. Hammering the screw into the bone carries a greater risk that the screw will become misaligned with the desired fixation location. Therefore, there is a need for a surgical screw that does not require the use of a pilot hole or a mallet, while maintaining sturdy and reliable fixation within the bone.

SUMMARY OF THE INVENTION

The present invention is directed to a surgical screw. The surgical screw comprises features for reducing the torque required to start or introduce the screw into the anatomy. According to one aspect, the surgical screw includes a cannulated body having a proximal end and a distal end. The distal end of the cannulated body can have a tapered tip, and a plurality of threads which can extend around the exterior of the cannulated body from a position at the very distal end, a position adjacent to the distal end, or a position proximal to the distal end to a position at the very proximal end, a position adjacent to the distal end, or a position distal of the proximal end. An introducer extends distally from the tapered tip and has a diameter (which can be constant or variable) which is less than a diameter of the tapered tip. The surgical screw is cannulated such that a channel extends through the body from the proximal end to the distal end.

According to another aspect, the surgical screw includes a cannulated body having a proximal end and a distal end, which has a tapered tip. A plurality of threads extend around the exterior of the cannulated body (from positions as described above). The plurality of threads include a primary thread and a secondary thread. A lead of the primary thread is greater than a pitch of the plurality of threads. An introducer extends distally from the tapered tip. The surgical screw is cannulated such that a channel extends through the body from the proximal end to the distal end.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
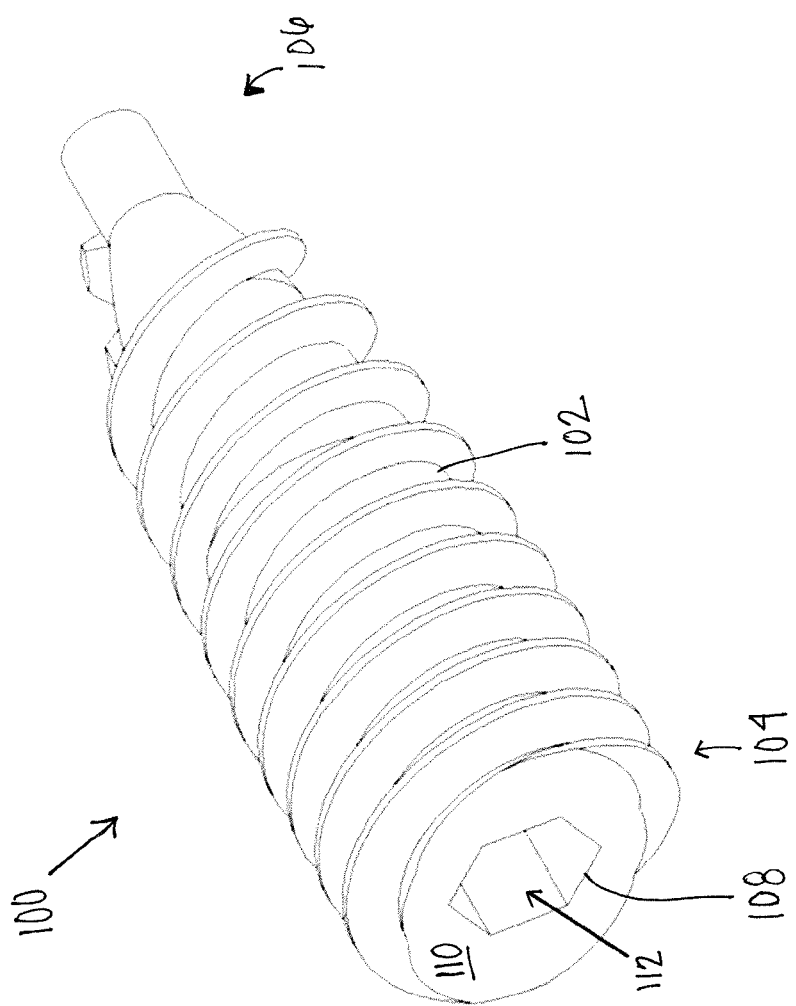
FIG. 1 is a proximal perspective view schematic representation of a surgical screw, according to an embodiment.

Referring now to the figures, wherein like reference numerals refer to like parts throughout, FIG. 1 shows a proximal perspective view schematic representation of a surgical screw 100, according to an embodiment. The surgical screw 100 comprises a body 102 extending between a proximal end 104 and a distal end 106. The surgical screw 100 can be composed of any suitable biocompatible material, such as titanium or magnesium, and can be manufactured according to common manufacturing methods, such as machining (as should be understood by a person of ordinary skill in the art in conjunction with a review of this disclosure). The surgical screw 100 may also be composed of bio-composite material and manufactured via injection molding (as should be understood by a person of ordinary skill in the art in conjunction with a review of this disclosure).

As shown in FIG. 1, the body 102 comprises a feature 108 at the proximal end 104 that allows the surgical screw 100 to be torqued. Specifically, the feature 108 is on an outer surface 110 of the proximal end 104. For example, the feature 108 can be that of any conventional screw head and non-conventional geometries as well (e.g., Tri-Lobe driver geometry). In the depicted embodiment, the feature 108 has a hexagonal cross-section. As shown in FIG. 1, the surgical screw 100 is cannulated such that a channel 112 extends from the feature 108 at the outer surface 110 of the proximal end 104 through the body 102 to the distal end 106.

Figure 2:
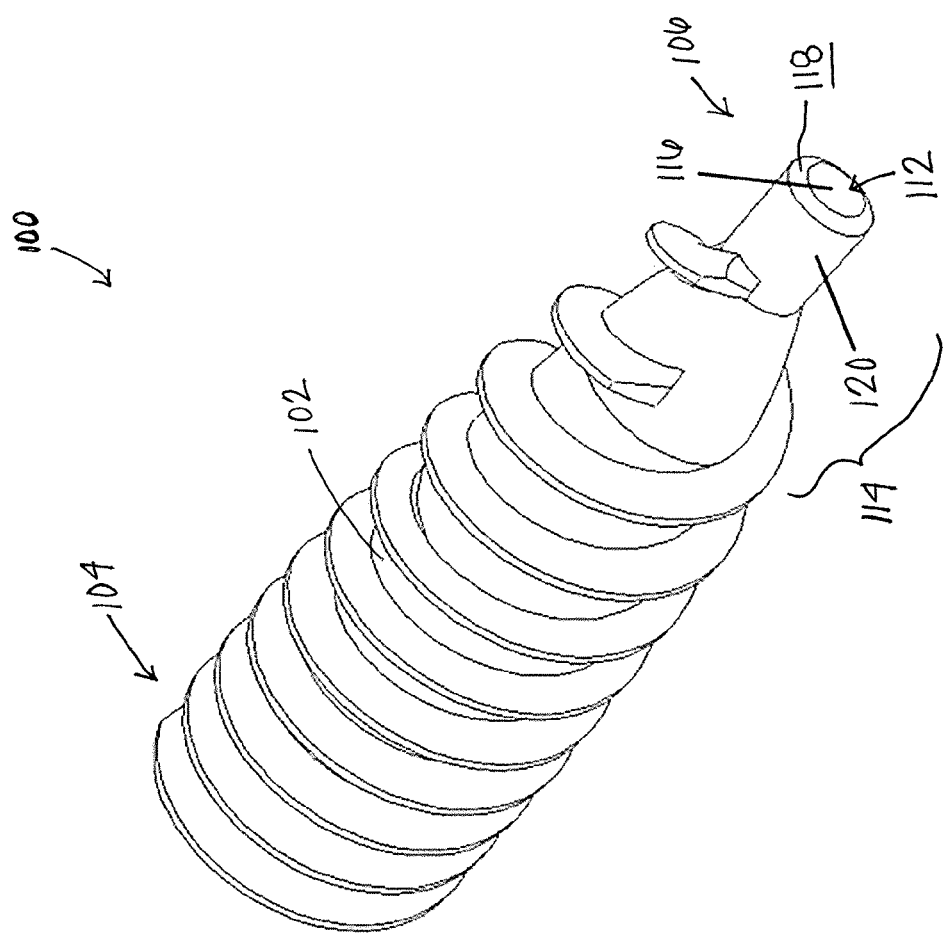
FIG. 2 is a distal perspective view schematic representation of a surgical screw, according to an embodiment.

Turning now to FIG. 2, there is shown a distal perspective view schematic representation of the surgical screw 100, according to an embodiment. In the depicted embodiment, the body 102 of the surgical screw 100 comprises a tip 114 at the distal end 106. In FIG. 2, the tip 114 is a tapered region (at least partially tapered, can be tapered all the way to the very distal end, and can include a constant, variable-increasing or decreasing taper, or more than one taper (which may be separated with a section with no taper) with the same or different taper value) such that the body 102 is tapered toward the distal end 106. As described above, the surgical screw 100 is cannulated. FIG. 2 shows the channel 112 extending through the body 102 of the surgical screw 100 to the tip 114 at the distal end 106. Specifically, the channel 112 extends from the feature 108 at the proximal end 104 to an opening 116 on an outer surface 118 of the tip 114.

Still referring to FIG. 2, the surgical screw 100 comprises an introducer 120 at the tip 114. In the depicted embodiment, the introducer 120 is an elongated extension from the tip 114. In the depicted embodiment, the introducer 120 is a narrow cylinder extending from the tip 114 at the distal end 106. As shown, the introducer 120 is also cannulated such that the introducer 120 has the outer surface 118 with the opening 116 to the channel 112 extending through the body 102. The introducer 120 allows for easier insertion of the surgical screw 100 because the introducer 120 can be used to align the surgical screw 100 at the desired bone hole location.

Figure 3:
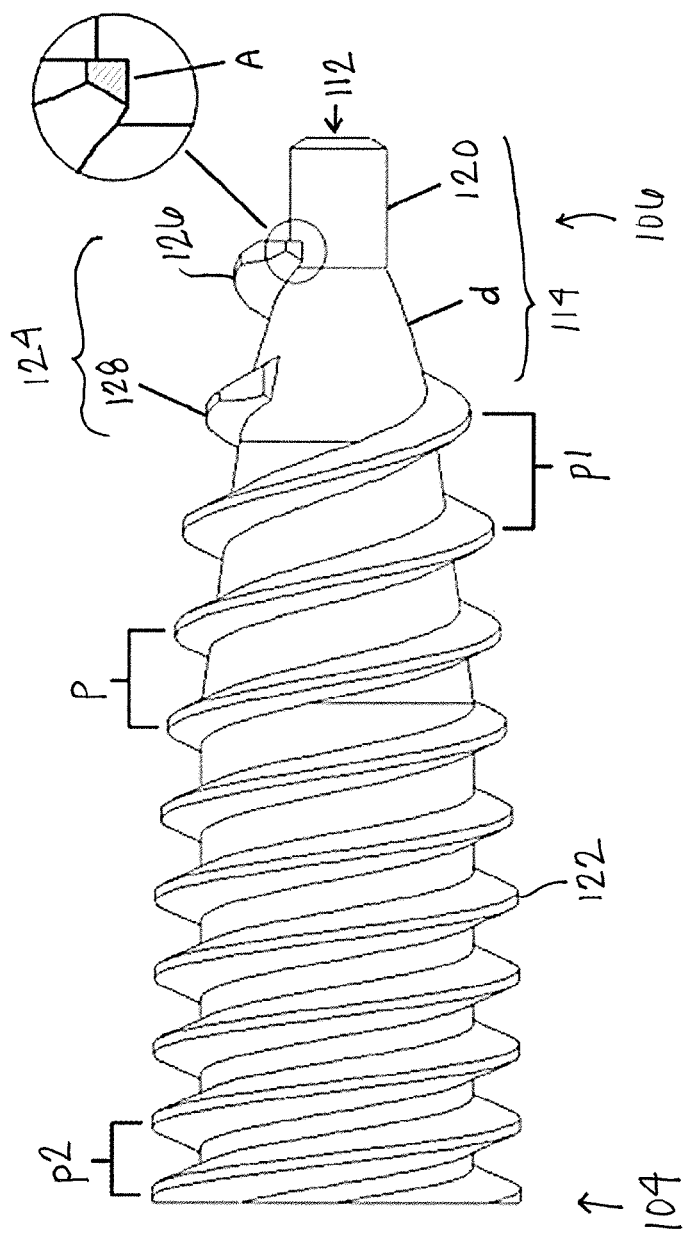
FIG. 3 is side view schematic representation of a surgical screw, according to an embodiment.

Referring now to FIG. 3, there is shown a side view schematic representation of the surgical screw 100, according to an embodiment. As shown in FIG. 3, the surgical screw 100 comprises a plurality of threads 122 along the length of the body 102. As with all conventional screws, adjacent threads 122 have a pitch p and root diameter d. However, the pitch p and therefore, the root diameter d of the depicted embodiment of the surgical screw 100 can be variable/non-constant (alternatively, the pitch can be variable and the root diameter can be constant or vice versa, and the pitch and/or the root diameter can be variable for a certain length of the body and constant for another length of the body). In other words, the threads 122 of the surgical screw 100 are not evenly spaced. In one embodiment, the pitch p increases from the proximal end 104 to the distal end 106, while the root diameter d increases from the distal end 106 to the proximal end 104. For example, as shown in FIG. 3, the pitch p1 at the distal end 106 is larger than the pitch p2 at the proximal end 104, and the root diameter at the distal end 106 is smaller than the root diameter at the proximal end 104.

Figure 12:
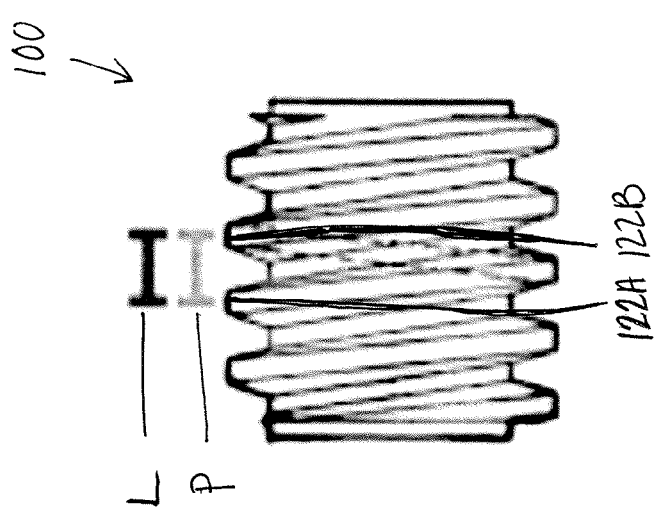
FIG. 12 is a close-up view schematic representation of an exemplary embodiment of a surgical screw with a single start.
Figure 13:
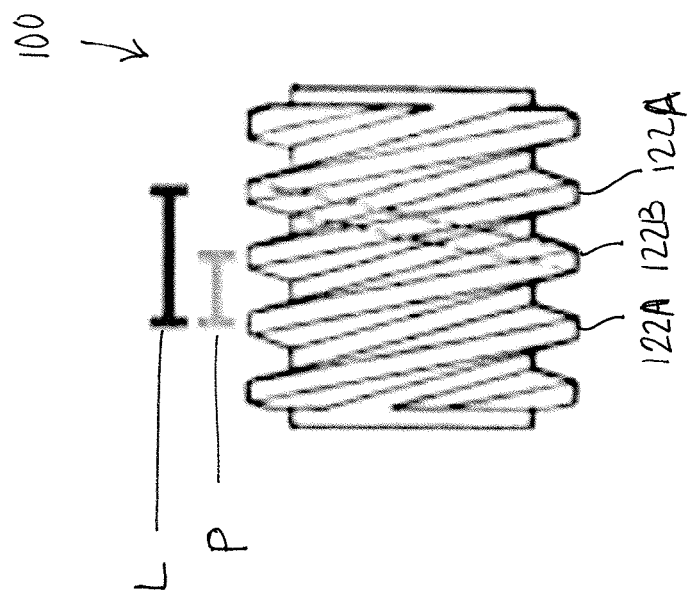
FIG. 13 is a close-up view schematic representation of an exemplary embodiment of a surgical screw with a double start.

Still referring to FIG. 3, the threads 122 of the surgical screw 100 are dual start threads. Dual start threads are two threads opposed at 180 degrees. As shown in FIG. 3, the surgical screw 100 comprises a staggered start 124. In other words, a secondary thread 128 begins 180 degrees later than a primary thread 126. As shown in FIG. 13, the primary thread 122A has a lead L, which is greater than the pitch p of the threads 122 (122A, 122B) when the surgical screw 100 has a dual start or staggered start 124. The surgical screw 100 may also have a triple start or any additional multiple start (as should be understood by a person of ordinary skill in the art in conjunction with a review of this disclosure, not shown) or a single start (FIG. 12) where the lead L and the pitch p are equal. In an embodiment, as shown in FIG. 3, the primary thread 126 has a reduced surface area A. The reduced surface area A reduces resistance and lowers torque during initial engagement with the bone.

Figure 4:
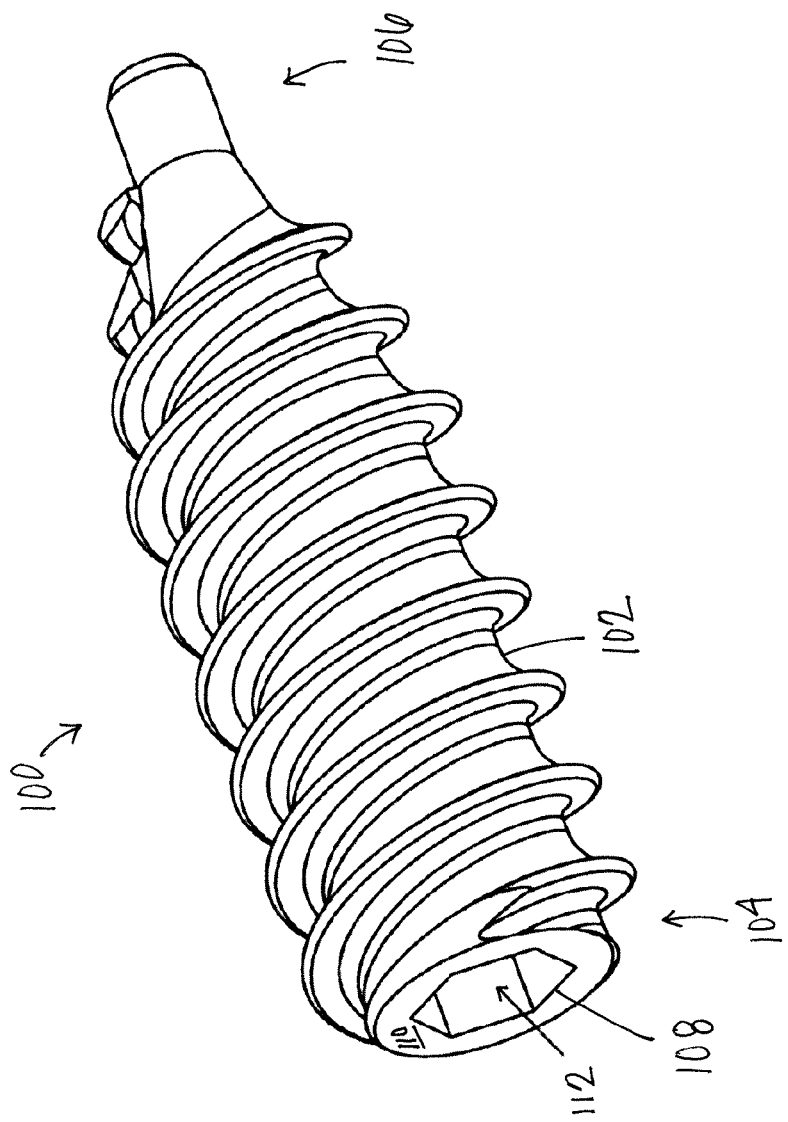
FIG. 4 is a perspective view schematic representation of a surgical screw, according to an alternative embodiment.

Turning now to FIGS. 4-11, there are shown various views schematic representations of surgical screw 100 according to alternative embodiments. First, in FIG. 4, there is shown a perspective view schematic representation of a surgical screw 100, according to an alternative embodiment. As with the surgical screw 100 in FIGS. 1-3, the surgical screw 100 in FIG. 4 comprises a body 102 extending between a proximal end 104 and a distal end 106 with a feature 108 on an outer surface 110 at the proximal end 104, which allows the surgical screw 100 to be torqued. As shown in FIG. 4, the surgical screw 100 is cannulated such that a channel 112 extends from the feature 108 at the outer surface 110 of the proximal end 104 through the body 102 to the distal end 106. As with the surgical screw 100 of FIGS. 1-3, the surgical screw 100 shown in FIGS. 4-11 can be composed of any suitable biocompatible material, such as titanium or magnesium, or bio-composite material, and can be manufactured according to common manufacturing methods, such as machining or injection molding, for example.

Figure 5:
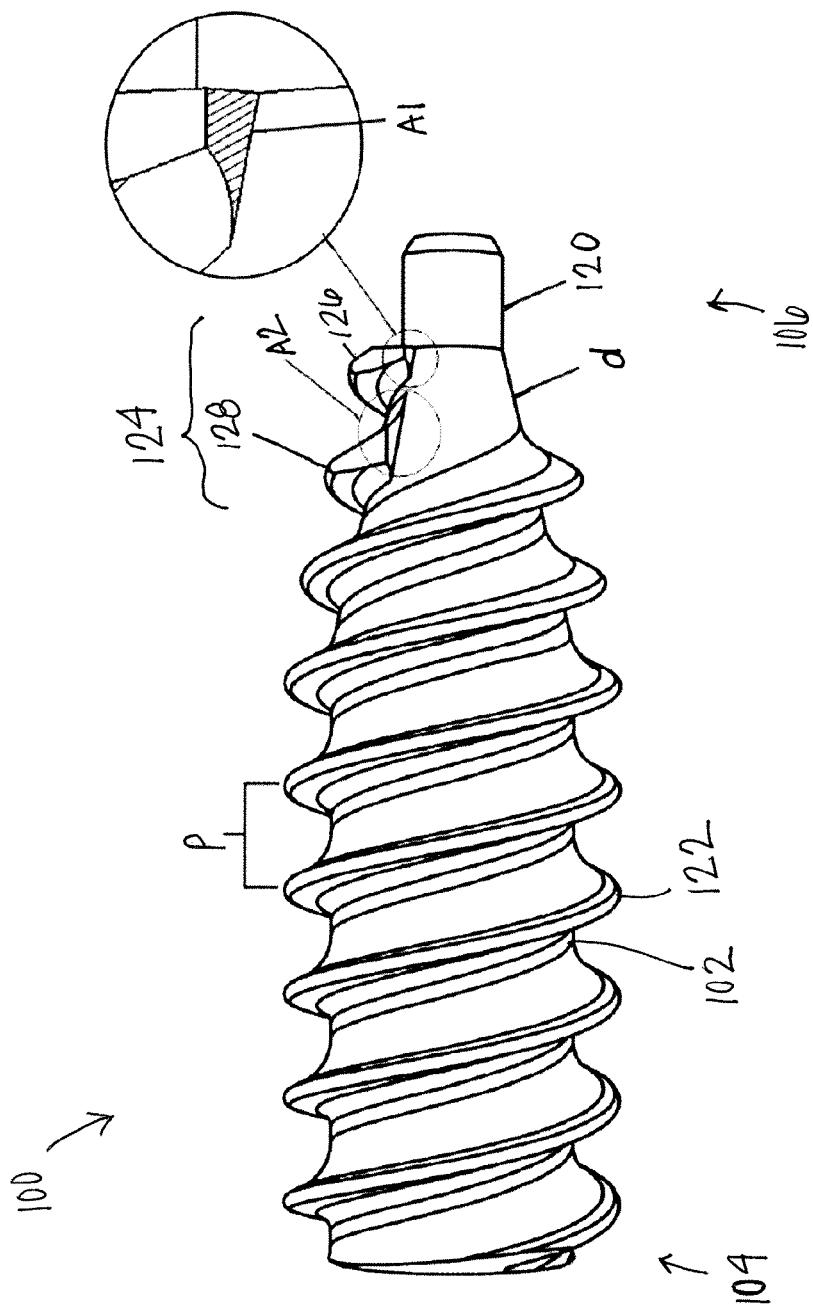
FIG. 5 is a side view schematic representation of a surgical screw, according to an alternative embodiment.

FIG. 5 shows a side view schematic representation of a surgical screw 100, according to an alternative embodiment. The surgical screw 100 shown in FIG. 5 has threads 122 extending along the body 102 of the screw 100. Adjacent threads 122 in the depicted embodiment have a constant (i.e., equal) pitch p. However, the surgical screw 100 may also have threads 122 with a variable pitch p1, p2, as shown in the embodiment in FIG. 3. The embodiment of the surgical screw 100 in FIG. 5 also has threads 122 with a root diameter d that is tapered from the proximal end 104 to the distal end 106. Specifically, the root diameter d decreases from the proximal end 104 to the distal end 106 (which can be a constant decrease in diameter in some embodiments, and a non-constant decrease in diameter in other embodiments).

Still referring to FIG. 5, the embodiment of the surgical screw 100 also includes a dual start thread (i.e., staggered start) 124. As stated above, the dual start thread 124 includes a primary thread 126, which is 180 degrees opposed from a secondary thread 128 such that the secondary thread 128 starts 180 degrees later (i.e., around the exterior of the body 102) than the primary thread 126. However, in other embodiments, the secondary thread 128 can start anywhere from a little as 5 degrees to as most as 360 degrees later than the primary thread 126. The primary thread 126 and secondary thread 128 have reduced surface areas A1, A2 to reduce resistance and lower torque during initial engagement with the bone.

Figure 6:
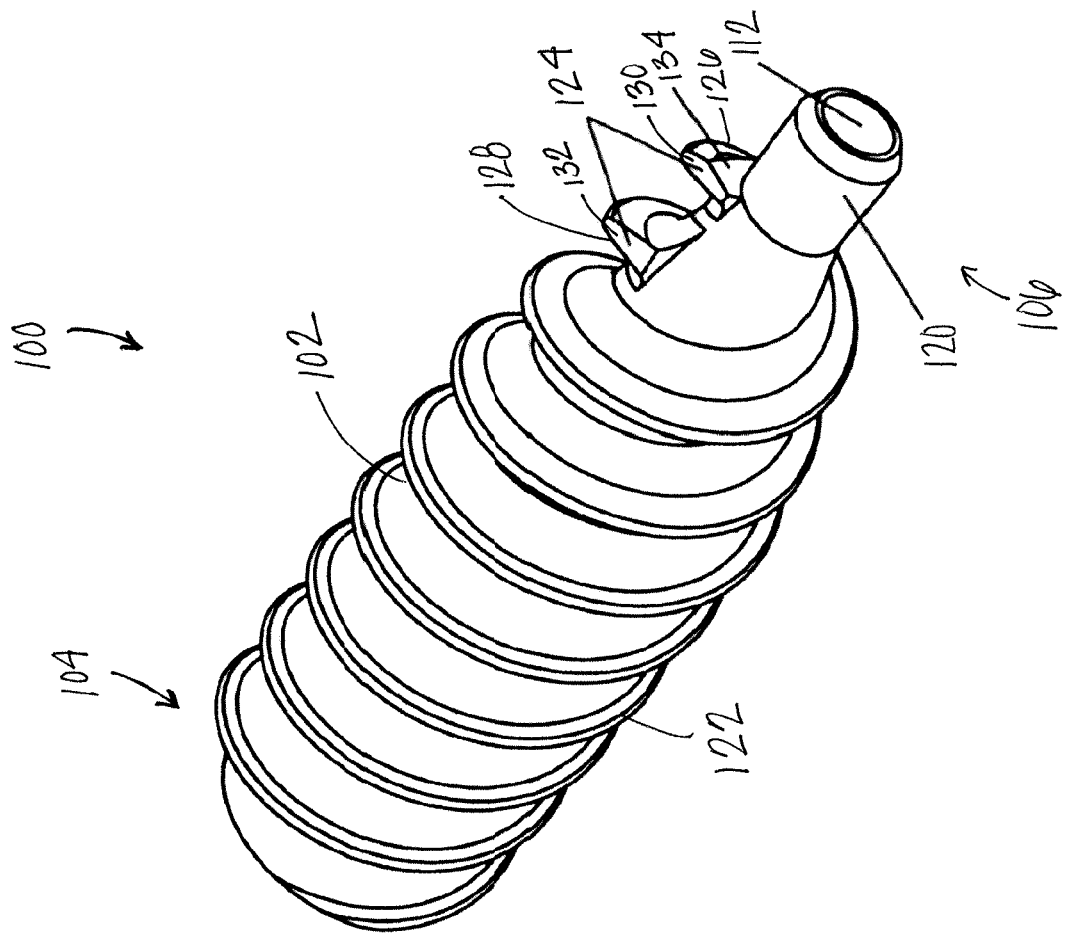
FIG. 6 is a distal perspective view schematic representation of a surgical screw, according to an alternative embodiment.
Figure 7:
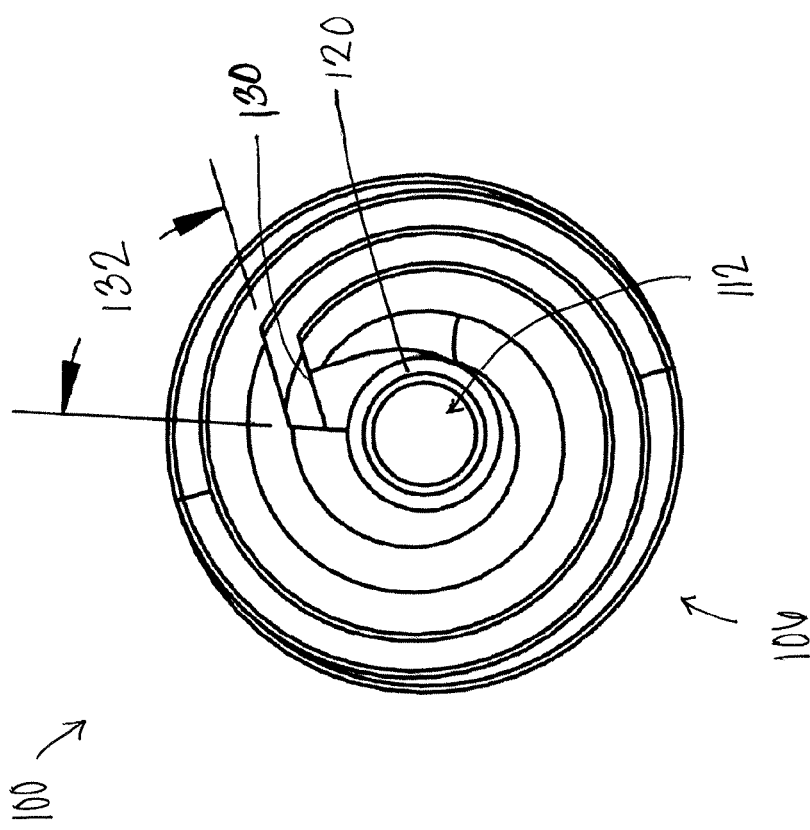
FIG. 7 is a distal end view schematic representation of a surgical screw, according to an alternative embodiment.

Turning now to FIGS. 6-7, there are shown distal end and distal perspective views schematic representations of a surgical screw 100, according to an alternative embodiment. In the depicted embodiment of the surgical screw 100, the primary thread 126 and the secondary thread 128 are chamfered. The chamfering removes a leading edge from the primary and secondary threads, further reducing the surface area A1, A2 thereof. As shown in FIG. 6, the chamfering creates a first sharp edge 130 on the primary thread 126 and a second sharp edge 132 on the secondary thread 128. The sharp edges 130, 132 allow for better engagement between the surgical screw 100 and bone. In the depicted embodiment, the distal portion 134 of the primary thread 126 is configured such that the surface area A1 of the primary thread 126 is further reduced as compared to the surface area A2 of the secondary thread 128. In additional embodiments, a radius is used in place of the chamfer when the surgical screw 100 is used for engagement with soft tissue as opposed to bone.

Figure 8:
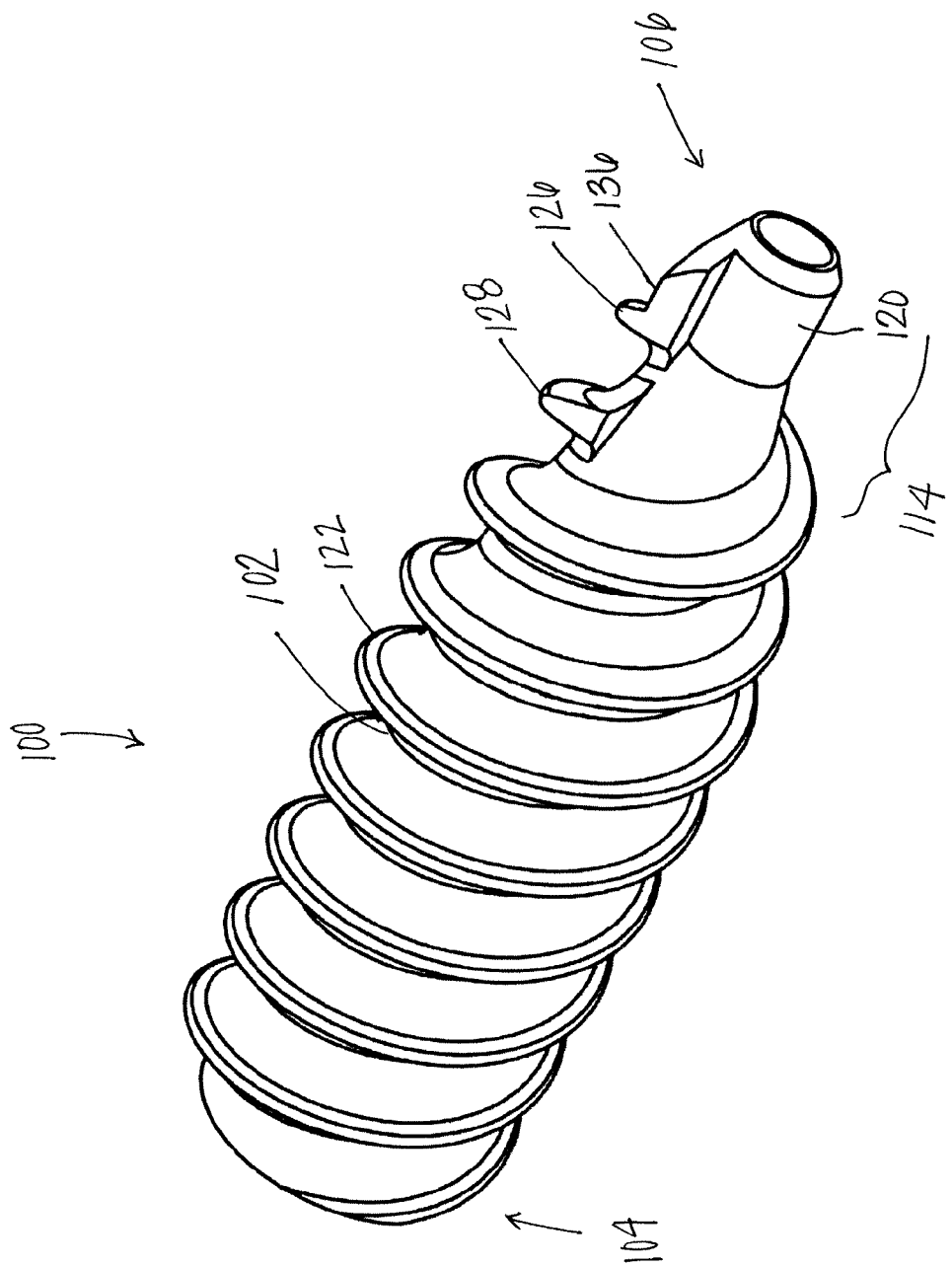
FIG. 8 is a distal perspective view schematic representation of a surgical screw, according to an embodiment.

Referring now to FIG. 8, there is shown a distal perspective view schematic representation of a surgical screw 100, according to an embodiment. In the depicted embodiment, the surgical screw 100 includes a notching feature 136 at the distal end 106. In one embodiment, as shown in FIG. 8, the notching feature 136 extends from the introducer 120 at the distal end 106 of the surgical screw 100. In the depicted embodiment, the notching feature 136 is a notch that extends approximately tangentially from the introducer 120. The notching feature 136 can be malleted into the bone when the bone is hard. For example, a surgeon will align the introducer 120 at the desired bone hole location and mallet the proximal end 104 of the surgical screw 100 such that the introducer 120 and notching feature 136 engage the bone. In another embodiment, the notching feature 136 is used to find gaps between a primary bone and a graft when the surgical screw 100 is rotated. When the notching feature 136 finds a gap, it directs the primary thread 126 to the desired area and the surgical screw 100 can be rotated and installed without the need for malleting.

Figure 9:
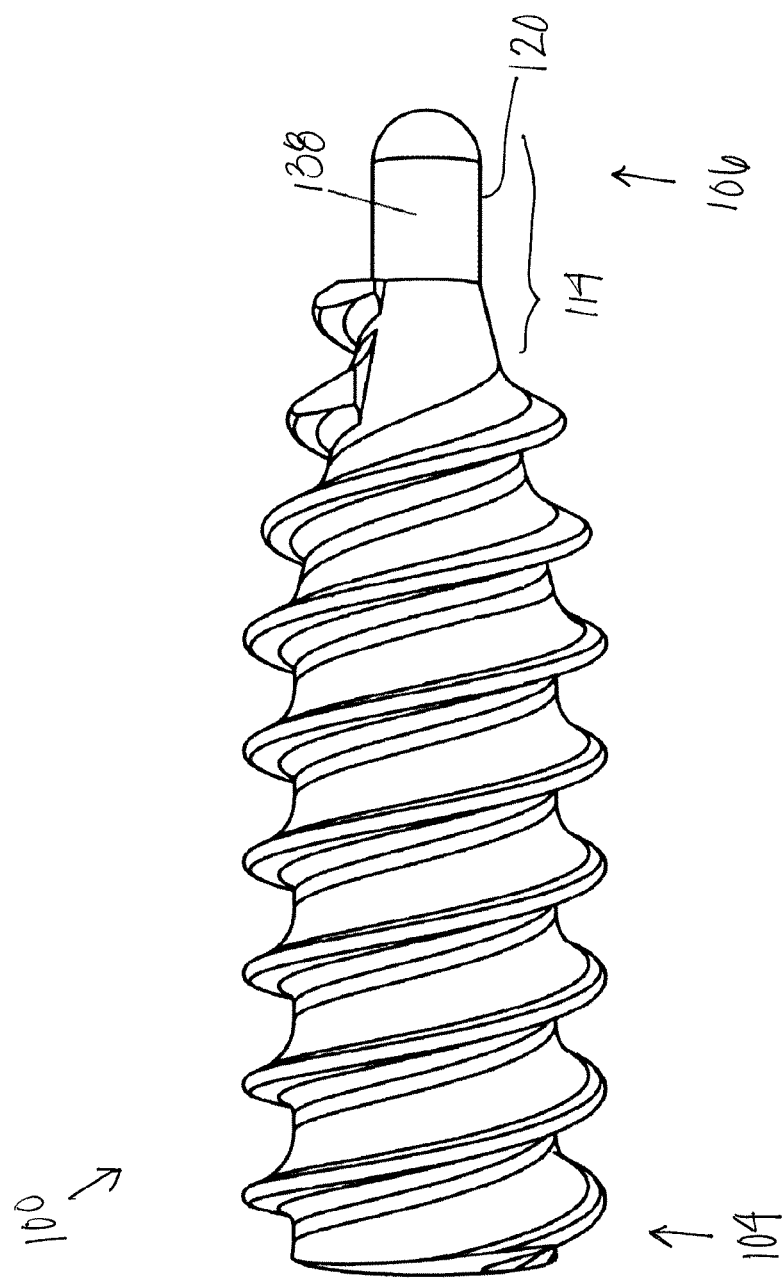
FIG. 9 is a side view schematic representation of a surgical screw, according to an alternative embodiment.
Figure 10:
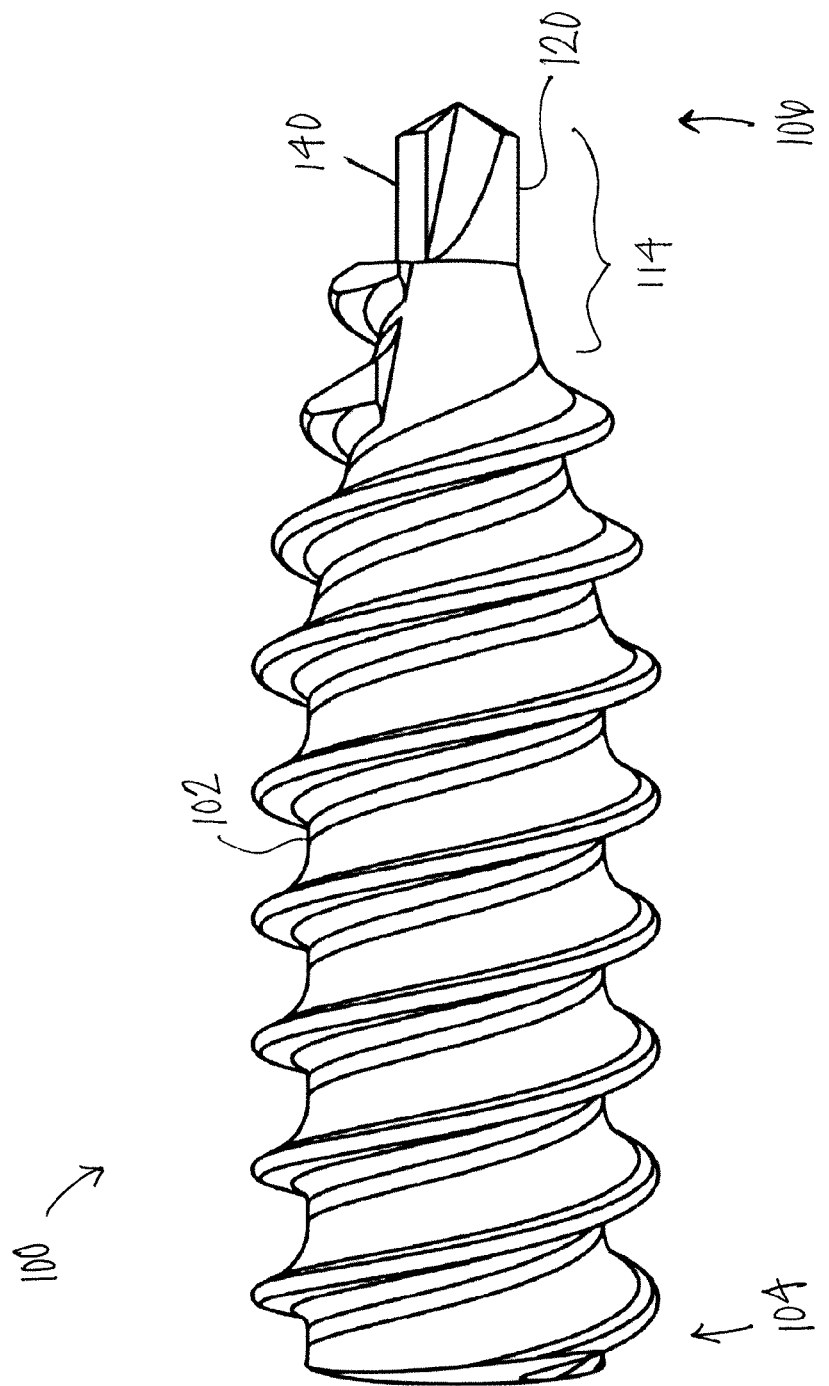
FIG. 10 is a side view schematic representation of a surgical screw, according to another embodiment.

Turning now to FIGS. 9-10, there are shown side views schematic representations of a surgical screw 100, according to additional embodiments. In the embodiment shown in FIGS. 9-10, the opening 116 to the channel 112 at the distal end 106 (introducer 120) of the surgical screw 100 is solid or otherwise replaced with a solid feature 138. The solid feature 138 may be rounded, as shown in FIG. 9, or the solid feature 138 may have any other suitable geometry. For example, the solid feature 138 may be a drill tip 140, as shown in FIG. 10. In the embodiments shown in FIGS. 9-10, the solid feature 138 is not cannulated. However, in alternative embodiments, the cannulation may also be completely removed (as in FIGS. 9-10) or only partially removed. In other words, the solid feature 138 can be either completely solid or only partially solid.

Figure 11:
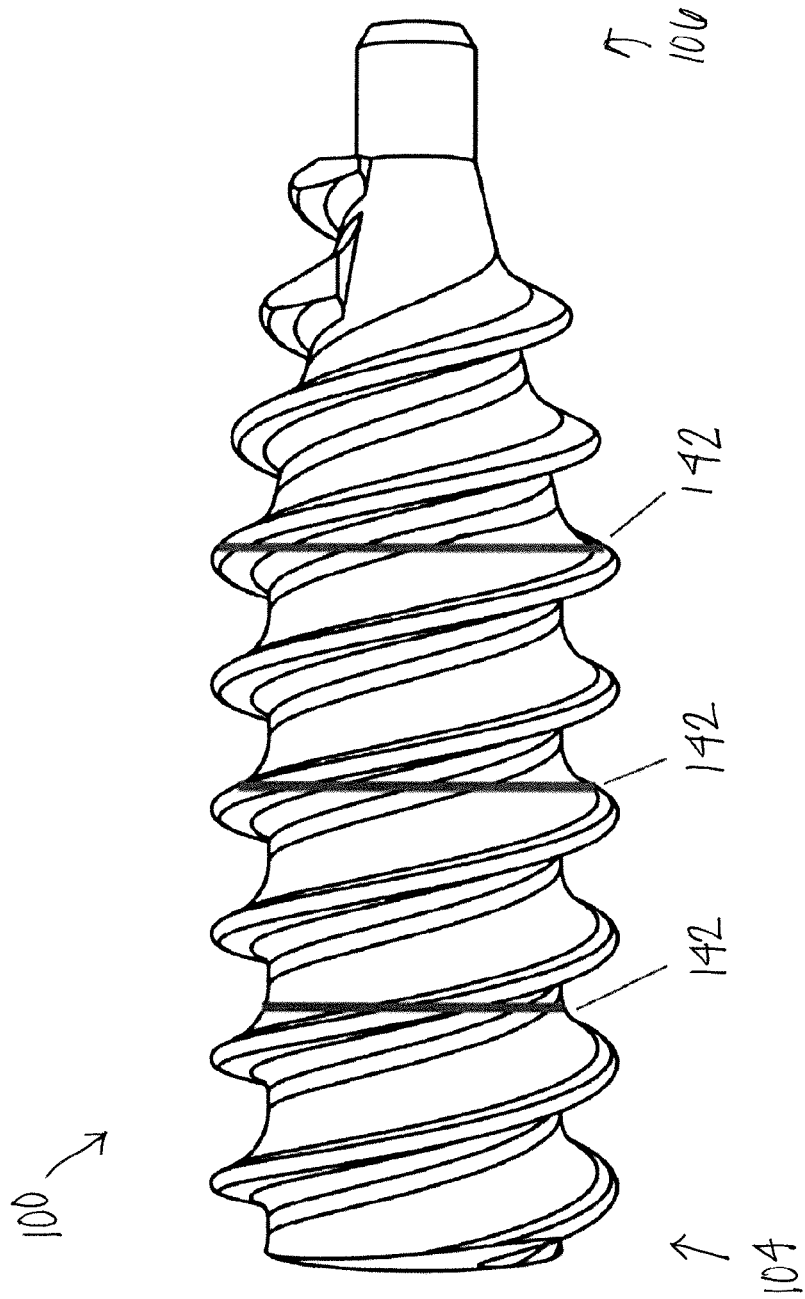
FIG. 11 is a side view schematic representation of a surgical screw, according to yet another embodiment.

Referring now to FIG. 11, there is shown a side view schematic representation of a surgical screw 100, according to yet another embodiment. In the depicted embodiment, the surgical screw 100 comprises one or more exterior markings 142 along the body 102 between the proximal end 104 and the distal end 106. The exterior markings 142 of the surgical screw 100 in FIG. 11 are depth indicator markings 142. The depth indicator markings 142 are visible to a surgeon (or other user) during rotation and installation of the surgical screw 100. The depth indicator markings 142 allow the surgeon to determine the depth of the surgical screw 100 within the bone or soft tissue. In the depicted embodiment, the depth indicator markings 142 are circumferential markings extending around the exterior of the surgical screw 100. However, the depth indicator markings 142 can be placed anywhere along the exterior of the surgical screw 100 such that they are visible to the surgeon (or other user). As shown in FIG. 11, the depth indicator markings 142 can include multiple markings 142 spaced at equidistant intervals (e.g., 5 mm), a single depth marking, or multiple markings spaced at irregular intervals, as desired, and can be made from or coated with radiographic material.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A surgical screw, comprising:
a cannulated body having a proximal end and a distal end, the distal end having a tapered tip;
a plurality of threads positioned around at least a portion of the exterior of the cannulated body;
an introducer extending distally from the tapered tip;
wherein the introducer has a diameter which is less than a greatest diameter of the tapered tip; and
a channel extending through the body from the proximal end to the distal end,
wherein the plurality of threads includes a primary external thread and a secondary external thread both positioned around at least the tapered tip,
wherein the primary external thread extends around the whole of the tapered tip region to the distal end of the tapered tip region, and
wherein the primary thread has a first edge with a first surface area at the tapered tip and the secondary thread has a second edge with a second surface area at the tapered tip, wherein the first surface area is less than the second surface area.

2. The surgical screw of claim 1, wherein the first edge of the primary external thread is chamfered.

3. The surgical screw of claim 2, wherein the second edge of the secondary external thread is chamfered.

4. The surgical screw of claim 1, wherein the first edge and the second edge are staggered on the tapered tip.

5. The surgical screw of claim 1, further comprising a notching feature extending from the introducer.

6. The surgical screw of claim 5, wherein the notching feature is a notch that extends approximately tangentially from the introducer.

7. The surgical screw of claim 1, wherein the cannulated body is composed of titanium.

8. The surgical screw of claim 1, wherein a lead of the primary thread is greater than a pitch of the plurality of threads.

9. The surgical screw of claim 1, wherein the primary thread and the secondary thread of the plurality of threads has a pitch, and each pitch is equal.

10. The surgical screw of claim 1, wherein the primary thread has a first pitch and the secondary thread has a second pitch, wherein the first pitch is greater than the second pitch.

11. The surgical screw of claim 1, wherein the primary thread and the secondary thread are opposed at an angle within the range of 5 degrees to 360 degrees.

12. The surgical screw of claim 11, wherein the primary thread and the secondary thread are opposed at about 180 degrees.

13. The surgical screw of claim 1, wherein the introducer is a cannulated cylinder.

* * * * *